(12) United States Patent
Kremers

(10) Patent No.: US 9,179,879 B2
(45) Date of Patent: Nov. 10, 2015

(54) MEDICAL COMPRESSION DEVICE

(76) Inventor: Peter W. Kremers, Frederick, MD (US)

( * ) Notice: Subject to any disclaimer, the term of this patent is extended or adjusted under 35 U.S.C. 154(b) by 847 days.

(21) Appl. No.: 13/285,377

(22) Filed: Oct. 31, 2011

(65) Prior Publication Data
US 2013/0072963 A1    Mar. 21, 2013

Related U.S. Application Data

(60) Provisional application No. 61/536,890, filed on Sep. 20, 2011.

(51) Int. Cl.
*A61B 6/04* (2006.01)
*A61B 17/12* (2006.01)
*A61B 17/00* (2006.01)
*A61B 19/08* (2006.01)
*A61B 10/02* (2006.01)
*A61B 19/00* (2006.01)

(52) U.S. Cl.
CPC ............. *A61B 6/0414* (2013.01); *A61B 6/0435* (2013.01); *A61B 10/02* (2013.01); *A61B 17/0057* (2013.01); *A61B 19/081* (2013.01); *A61B 2017/12004* (2013.01); *A61B 2019/205* (2013.01)

(58) Field of Classification Search
CPC .. A61B 10/02; A61B 17/0057; A61B 19/081; A61B 2017/12004; A61B 6/0414; A61B 6/0435

USPC .................... 606/157, 158, 201–204, 204.15
See application file for complete search history.

(56) References Cited

U.S. PATENT DOCUMENTS 3,884,240 A * 5/1975 Gilman .......................... 606/201
4,182,338 A * 1/1980 Stanulis ........................ 606/203
(Continued)

FOREIGN PATENT DOCUMENTS

AU    2008 201 638 A1    5/2008
WO    WO 93-17620 A1    9/1993

OTHER PUBLICATIONS

International Search Report and Written Opinion of the International Searching Authority for PCT/US2012/056183 mailed Mar. 6, 2013.
(Continued)

*Primary Examiner* — Julian W Woo
(74) *Attorney, Agent, or Firm* — Nixon & Vanderhye, P.C.

(57) ABSTRACT

A device is provided that aids in the medical compression process. One example of such a device is a medical compression device that can be added to medical machinery, such as the Hologic® Multicare Prone Biopsy table or a Hologic® upright biopsy table/system. The device can be configured to be placed into and partially through an "operating window" of a compression paddle component used in the biopsy table. The device advantageously does not require modification of the biopsy table or modification of the compression paddle/guide for use.

22 Claims, 13 Drawing Sheets

(56) References Cited

U.S. PATENT DOCUMENTS

| | | | |
|---|---|---|---|
| 4,943,986 A | | 7/1990 | Barbarisi |
| 5,040,198 A | | 8/1991 | Hixson, Sr. |
| 5,136,623 A | * | 8/1992 | Hixson, Sr. ............... 378/37 |
| 5,290,307 A | * | 3/1994 | Choy ...................... 606/204 |
| 5,295,996 A | * | 3/1994 | Blair ...................... 606/203 |
| 5,541,972 A | | 7/1996 | Anthony |
| 5,595,177 A | | 1/1997 | Mena et al. |
| 7,319,734 B2 | | 1/2008 | Besson et al. |
| 7,489,761 B2 | | 2/2009 | Defreitas et al. |
| 2004/0039413 A1 | * | 2/2004 | Akerfeldt et al. ............. 606/201 |
| 2005/0008117 A1 | | 1/2005 | Livingston |
| 2005/0113684 A1 | | 5/2005 | Lokhandwalla et al. |
| 2006/0126794 A1 | | 6/2006 | Hermann et al. |

OTHER PUBLICATIONS

International Preliminary Report on Patentability for PCT/US2012/056183 mailed Apr. 3, 2014.
Extended European Search Report dated Jul. 23, 2015 for European Application No. EP12 83 4031.

* cited by examiner

MEDICAL COMPRESSION DEVICE

RELATED APPLICATION

This application claims the benefit of priority to U.S. Provisional Patent Application No. 61/536,890 filed Sep. 20, 2011, the entirety of which is hereby incorporated herein by reference.

BACKGROUND AND SUMMARY OF EXAMPLE EMBODIMENTS

Certain medical procedures can cause many unwanted side effects. For example, bleeding with the development of a hematoma after minimally invasive breast biopsies performed with stereotactic guidance can have a significant negative impact on patient satisfaction and may complicate and delay definitive post procedure care.

For example, large post biopsy hematomas can distort regional breast anatomy at the biopsy site and lead to significant delays of up to six weeks in performing lumpectomy for biopsy proven small breast cancers due to distortion and displacement of the tumor site. Large or painful post biopsy hematomas can also lead to reluctance in patients to undergo future medical interventions including recommended breast biopsies. Furthermore, post procedure hematomas may also increase post biopsy infection rates and, for some patients, the pain and delay in treatment may alter negatively the relief that a curable cancer was accurately diagnosed with the biopsy.

Currently, a breast biopsy may be performed by medical personnel using a variety of different modalities employing ultrasound, MRI or stereotactic guidance. For example, medical personnel may use a machine-operated unit to perform the biopsy using digital X-ray and stereotactic targeting techniques followed by manual compression of the biopsy site to prevent bleeding and hematoma formation.

One example of such a unit is the Hologic® MultiCare Prone Biopsy table or a Hologic® upright biopsy table/system. With the prone biopsy table, a patient lies prone on the biopsy table with her breast pendulant thru a hole in the table. Medical personnel may then target and perform a breast biopsy and other related procedures. Typically, a medical technologist or nurse will then apply manual compression to the biopsy site of the patient as part of a medical procedure to limit bleeding and hematoma development.

Currently, manual compression after biopsies requires valuable medical technologist or nursing time averaging 10 to 15 minutes per case and up to 40 minutes in more difficult cases if persistent bleeding is noted or the patient is on "blood thinners"/anticoagulant therapy. The degree, effectiveness, and duration of manual compression are variable among medical personnel potentially leading to bleeding and hematoma formation.

Hematomas are difficult to control once they have evolved and hence early effective compression preventing hematomas from developing is desirable.

There is thus an opportunity to improve the existing technology, especially with respect to medical manual compression procedures.

In certain example embodiments, a device is provided that aids in the medical compression process. One example of such a device is a medical compression device that can be added to medical machinery, such as the Hologic® Multicare Prone Biopsy table, for example. The device can be configured to be placed into and partially through an "operating window" of a compression paddle component used in the biopsy table. The device advantageously does not require modification of the biopsy table or modification of the compression paddle/guide for use.

In another example embodiment, the medical compression device can be affixed to the "operating window" of the compression paddle component by using a latch design to fasten the device to the paddle. The medical compression device may also be affixed to the "operating window" without the use of latches also. For example, the medical compression device may have a grooved portion that is configured to allow the device to be affixed to the "operating window" of the compression paddle without the use of latches.

BRIEF DESCRIPTION OF THE DRAWINGS

These and other features and advantages may be better and more completely understood by reference to the following detailed description of exemplary illustrative embodiments in conjunction with the drawings, of which:

FIGS. 3a-1 and 3a-2 are diagrams of an example embodiment of a medical compression device;

FIGS. 3b-1 and 3b-2 are diagrams of an example embodiment of the medical compression device using an example interchangeable face component;

FIGS. 3d-1 and 3d-2 are further diagrams of another example embodiment of the medical compression device having a large flat face;

DETAILED DESCRIPTION OF CERTAIN EXAMPLE EMBODIMENTS

Figure 1:
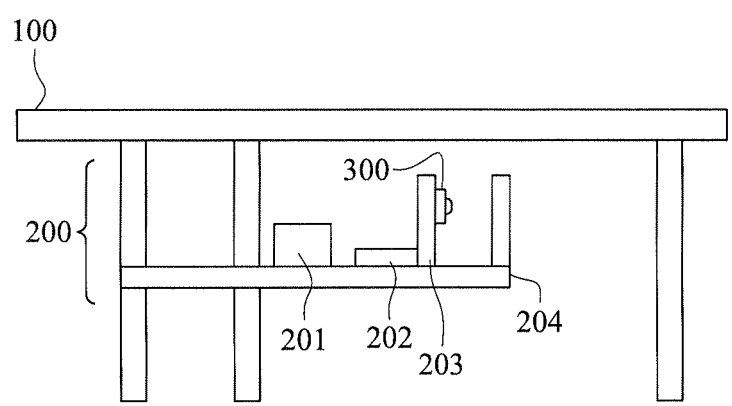
FIG. 1 is a diagram showing an example embodiment of a biopsy table using a medical compression device.

In the following description, for purposes of explanation and non-limitation, specific details are set forth, such as particular nodes, functional entities, techniques, protocols, standards, etc. in order to provide an understanding of the described technology. It will be apparent to one skilled in the art that other embodiments may be practiced apart from the specific details described below. In other instances, detailed descriptions of well-known methods, devices, techniques, etc., are omitted so as not to obscure the description with unnecessary detail. Individual function blocks are shown in the figures. Those skilled in the art will appreciate that the functions of those blocks may be implemented using individual hardware circuits, using software programs and data in conjunction with a suitably programmed microprocessor or general purpose computer, using applications specific integrated circuitry (ASIC), and/or using one or more digital signal processors (DSPs). The software program instructions and data may be stored on non-transitory computer-readable storage medium and when the instructions are executed by a computer or other suitable processor control, the computer or processor performs the functions. Although databases may be depicted as tables below, other formats (including relational databases, object-based models and/or distributed databases) may be used to store and manipulate data.

Although process steps, algorithms or the like may be described or claimed in a particular sequential order, such processes may be configured to work in different orders. In other words, any sequence or order of steps that may be explicitly described or claimed does not necessarily indicate a requirement that the steps be performed in that order. The steps of processes described herein may be performed in any order possible. Further, some steps may be performed simultaneously despite being described or implied as occurring non-simultaneously (e.g., because one step is described after the other step). Moreover, the illustration of a process by its depiction in a drawing does not imply that the illustrated process is exclusive of other variations and modifications thereto, does not imply that the illustrated process or any of its steps are necessary to the invention(s), and does not imply that the illustrated process is preferred. A description of a process is a description of an apparatus for performing the process. The apparatus that performs the process may include, e.g., at least one processor and those input devices and output devices that are appropriate to perform the process.

Various forms of computer readable media may be involved in carrying data (e.g., sequences of instructions) to a processor. For example, data may be (i) delivered from RAM to a processor; (ii) carried over any type of transmission medium (e.g., wire, wireless, optical, etc.); (iii) formatted and/or transmitted according to numerous formats, standards or protocols, such as Ethernet (or IEEE 802.3), SAP, ATP, Bluetooth, and TCP/IP, TDMA, CDMA, 3G, etc.; and/or (iv) encrypted to ensure privacy or prevent fraud in any of a variety of ways well known in the art.

The technology described herein improves upon the existing medical technology, especially with respect to compression procedures. In particular, the technology described herein can reduce human error by providing effective, constant, and durable compressive force on post-biopsy sites.

Current manual compression is susceptible to predictable user error. In particular, users often apply inconsistent pressure of less than optimal duration and force due to user fatigue. For example, the Hologic® prone biopsy table design and patient orientation requires the medical personnel to apply pressure on the biopsy site while they are seated with their arms above their heads. One can appreciate that this is a difficult position to maintain even if only for ten to fifteen minutes, but is especially tiring in cases with difficult to control bleeding sites requiring compression for twenty or more minutes. Likewise, manual compression of thick dense breasts or sites deep within the breast is also physically demanding and prone to diminished optimal pressure applied over time due to user fatigue.

The technology described herein aids users of this equipment by improving the compression techniques. For example, the design characteristics of the medical compression device offer several contours to focus optimal pressure on biopsy sites depending on the location of the biopsy site in the posterior, mid, or anterior breast.

One example design is a slanted or "off-set" design surface contour that is reversible in its attachment to the compression paddle. The "off-set" design option allows for centered compression on biopsy sites at the posterior-most locations reachable by the stereotactic table. Alternatively, when reversed, the "off-set" design stabilizes the mid-breast area to allow for pressure on anterior sites close to the nipple of the breast, for example.

Another example design involves a smaller focus contour design. With the smaller focus contour design, a modified half-sphere is used that allows for more optimal focused pressure in the mid or deep breast and for more optimal focused compression in patient's with dense or thick breasts.

Yet another example design involves a flat surface. Using the flat surface, a larger, less focused field of compression can be applied if more than one biopsy site is to be compressed simultaneously. It should be appreciated that the faces of the medical compression device may be interchangeable or may be manufactured as a single, whole component. For example, the medical compression device may be assembled so that three or more different devices are available as single, whole units, each having different faces, as mentioned above.

Although actual dimensions for the medical compression device are not discussed in detail in this specification, certain images showing various dimensions of the device are available in U.S. Provisional Patent Application No. 61/536,890 to which this application claims priority. All images and descriptions discussed therein are hereby incorporated by reference. Of course, the medical compression device is in no way limited to any dimensions shown in Application No. 61/536,890 and the medical compression device can be designed/configured to have a variety of different dimensions.

FIG. 1 shows a diagram of an example embodiment of a medical system 1 using medical machinery that incorporates the present technology. The system 1 has a table 100 that, for example, a patient may lie on while a procedure is being performed on the patient. The system 1 also has medical equipment 200 that performs medical procedures on the patient.

The medical equipment 200 has a controller 201, a motion control device 202, a compression paddle 203, and a compression plate 204. The controller 201 can operate the medical equipment 200. For example, the controller 201 can move the compression paddle 203 closer to or farther from the compression plate 204 by directing the motion control device 202 as to where to move. The controller 201 can be configured to have one or more processors, one or more memories, one or more input/output devices, and/or one or more networking components.

Although not limited to this embodiment, the compression paddle 203 utilizes a medical compression device 300. As explained further below, the medical compression device 300 can be affixed to the paddle 203 in a variety of ways.

Figure 2A:
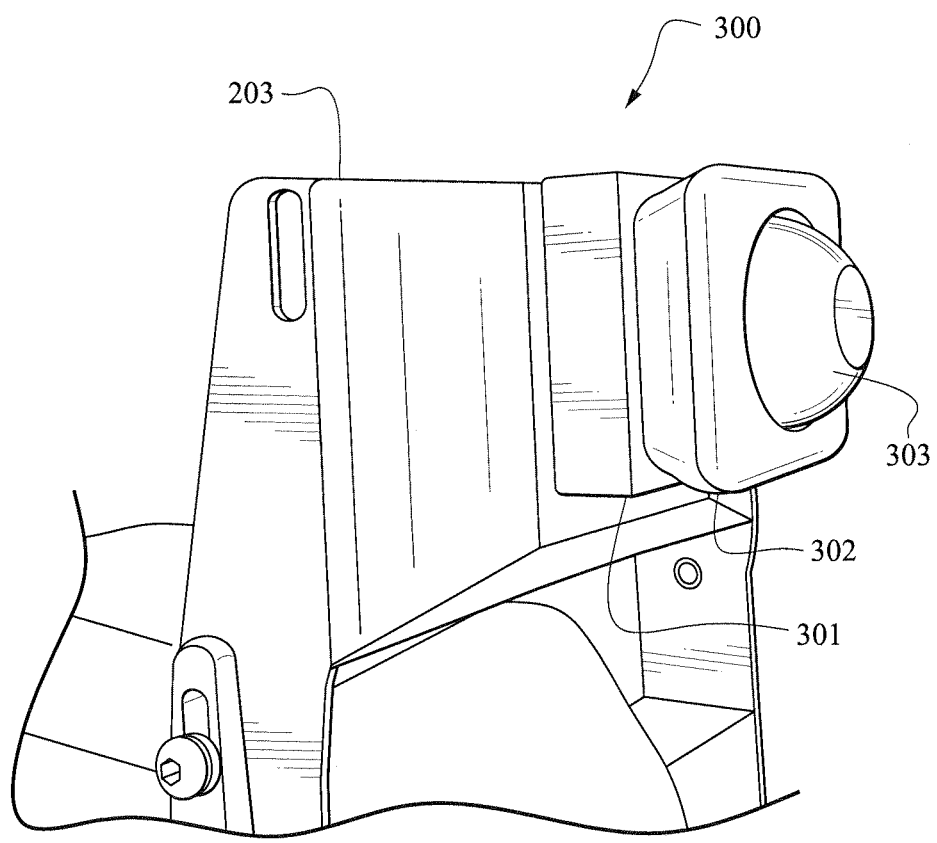
FIG. 2a is an exploded view of a diagram of an example embodiment of the medical compression device used in the biopsy table.

FIG. 2a shows an image of an exploded view of an example embodiment of the medical compression device 300 used in paddle 203. In this view, the medical compression device 300 has a base portion 301 and a front surface 302. Also shown in this image is a removable portion 303. Although not limited to this embodiment, the removable portion 303 can be a half-sphere shape and can be attached to/removed from the front surface 302 by using magnets, for example.

The compression device 300 provides one advantage of allowing the operator to focus the compression technique on a particular area of the patient's anatomy. As discussed further below, different compression devices 300 having different front surfaces 302 can be used depending upon the nature of the medical procedure and/or the patient's anatomy. It should also be appreciated that the device 300 can be configured to fit any size of paddle 203 and is not limited to the paddle 203 shown in these examples.

Figure 2B:
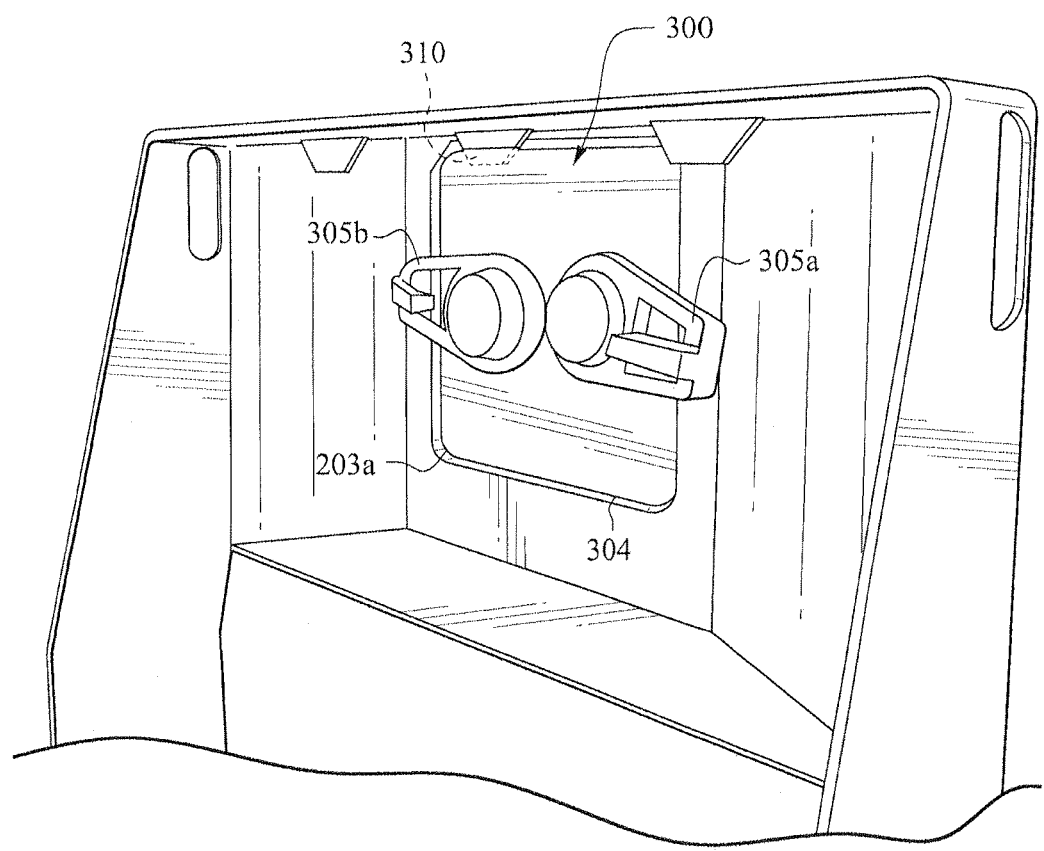
FIG. 2b is an exploded view of another diagram of an example embodiment of the medical compression device used in the biopsy table.

FIG. 2b depicts another image of an exploded view of an example embodiment of the medical compression device 300 used in the paddle 203. In this example, a view of the back of the paddle 203 is shown. As can be better seen in this image, the paddle 203 has a window 203a that allows a user to better operate the paddle 203. In certain applications, the window 203a may be filled with a component, such as a plastic face for allowing the user to view the patient's anatomy being compressed.

In FIG. 2b, the window 203a is configured to use the medical compression device 300. In this view, the medical compression device 300 has a back surface 304 that is configured to use latches 305a and 305b. It should be appreciated that this configuration is not limited to using two latches and can use any number of latches. Likewise, the device 300 can be affixed to the paddle 203 without using latches. It should also be appreciated that the back surface 304 can have contours and/or grooves to allow the device to be affixed to a paddle 203 that may have a non-uniform rectangular window 203a. That is, should the window 203a have a metallic edge extending from a top of the window 203a, the back surface 304 can be designed with a special groove to fit within the edge extending from the top of the window 203a.

Here, the latches 305a, 305b overlap a portion of the paddle 203 so that the weight of the device 300 pulls the device forward but is held in place by the secured latches 305a, 305b on the back surface 304 of the base portion 301. That is, the latches 305a, 305b fasten the device 300 to the paddle 203 by overlapping portions of the paddle 203 and the device 300 so that the device 300 will not fall out of the window 203a.

Also shown in FIG. 2b is a notch portion 310. It should be appreciated that the window 203a of the paddle 203 may not be entirely uniform in area (i.e. a perfect square). That is, the window may have portions that "jut" out and make it difficult to affix the device 300 to the window. In that event, the device 300 can be configured to have the notch portion 310 so that the device 300 will still fit uniform in the window 203a. Of course, this is a modification of the device 300 and the device 300 can be configured in any manner that allows it to be affixed to the window 203a of the paddle 203.

Figure 2C:
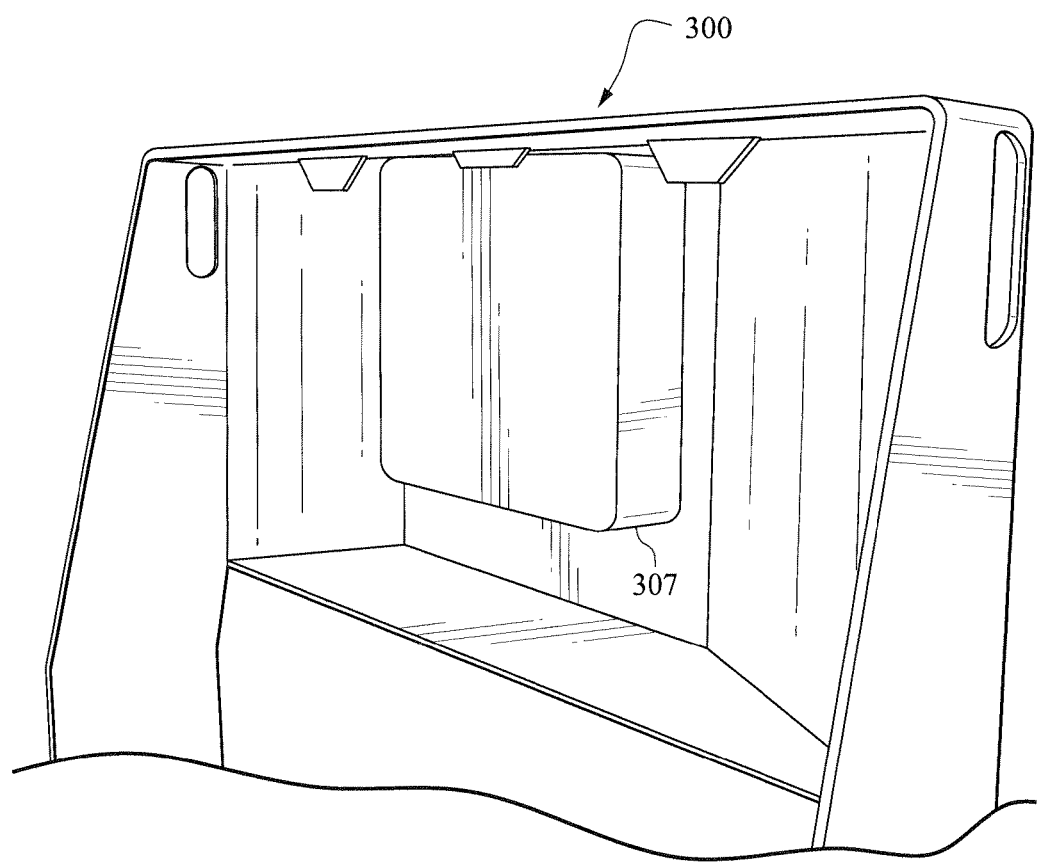
FIG. 2c shows another exploded view of a diagram of an example embodiment of another medical compression device used in the biopsy table.

FIG. 2c shows a diagram of another example embodiment of a view of the back surface of the medical compression device 300 in the paddle 203. This diagram shows the medical compression device 300 without the use of the latches 305a, 305b. Here, the device 300 is configured to use an attachment portion 307 and the attachment portion 307 is secured around the surface of the back side of the paddle 203. As explained further below, the device 300 can attach to the paddle 203 without using latches by having grooves in the device 300 for sitting in the window 203a of the paddle 203.

Figure 2D:
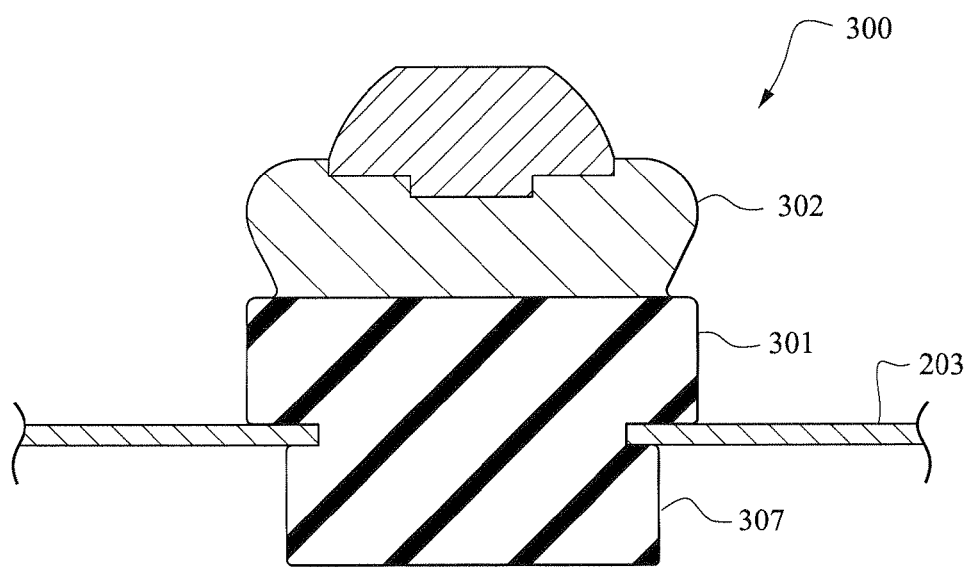
FIG. 2d depicts a cross-sectional view of an example embodiment of the medical compression device used in the biopsy table.

FIG. 2d shows a diagram of a cross-sectional view of the device 300 in the paddle 203. As can be seen in FIG. 2d, the device 300 has grooves (explained further below) that allow the device 300 to sit within the window 203a of the paddle 203. In an example embodiment, the attachment portion 307 will be smaller in width than the base portion 301 but larger in width and/or area than the window 203a so that the device can securely fit within the window 203a. A user can, for example, angle the device 300 so that the attachment portion 307 can be inserted into the window 203a and the device 300 will essentially sit in the window 203a by having the paddle 203 fill the grooves in the device, as can be seen in FIG. 2d.

Figures 1, 3A:
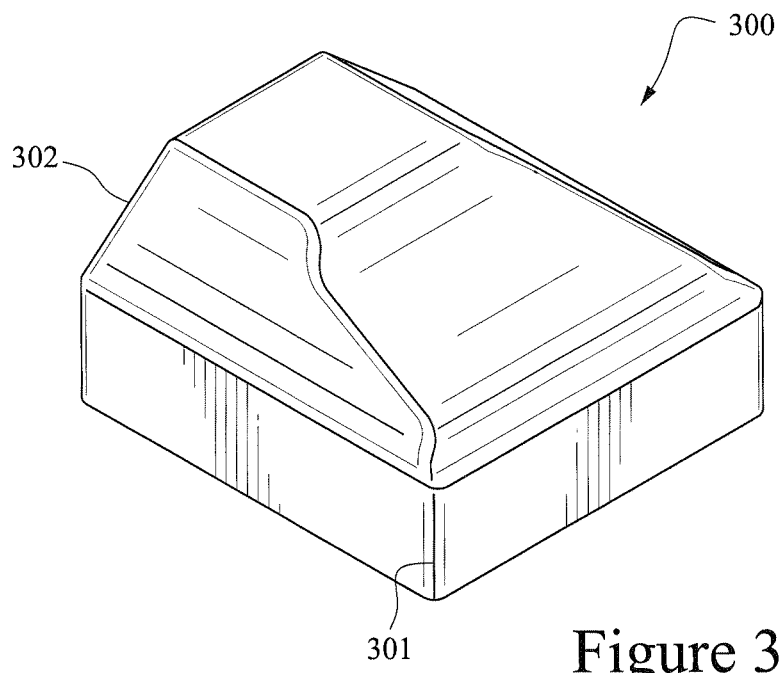
Figures 2, 3A:
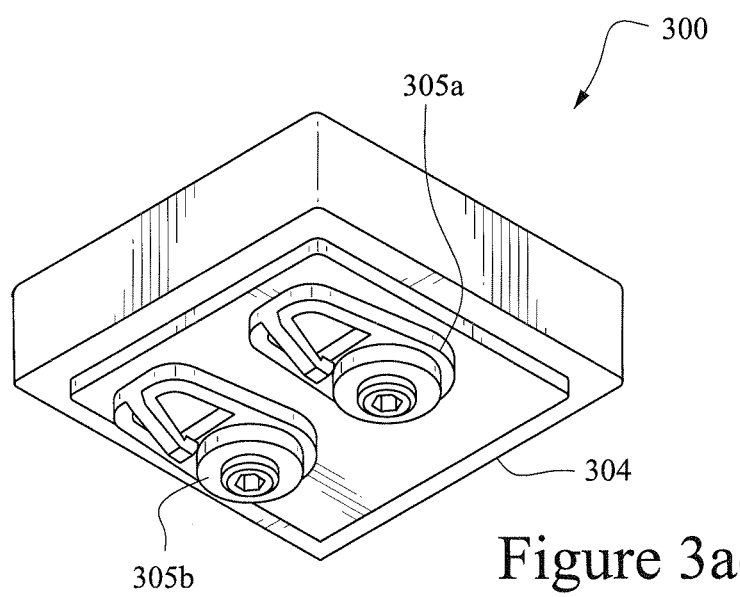

FIGS. 3a-1 and 3a-2 depict diagrams showing a certain example embodiment of the medical compression device 300. In FIGS. 3a-1 and 3a-2, both the front surface 302 and the back surface 304 are shown thereby showing both the front and back views of the device 300. As seen previously in FIG. 2b, this embodiment of the device 300 has latches 305a, 305b on the back surface 304 for connecting the device 300 to the paddle 203.

In the example shown in FIG. 3a-1, the front surface 302 is a non-interchangeable, contoured surface. For example, the front surface 302 can be characterized as an "off-set" or "slanted" compression contour. Such a design can be useful because it allows for centered compression on biopsy sites at the posterior-most locations reachable by a stereotactic table. This design may also be inserted in different positions into the window 203a. That is, the device 300 may be inserted such that the contoured portion is at the top, bottom, left, or right as it is used in the compression process. Of course, the design is one of many ways in which the front surface 302 of the device 300 can be configured.

Figures 1, 3B:
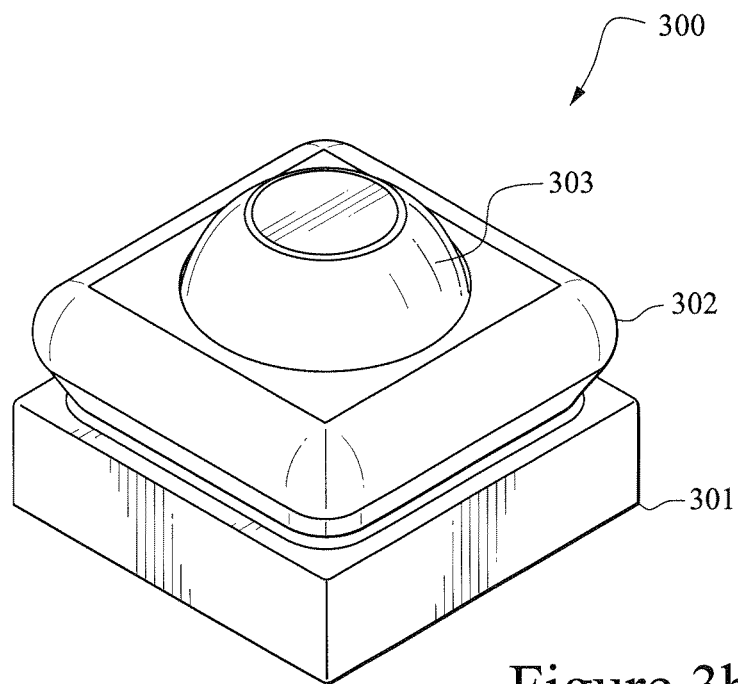
Figures 2, 3B:
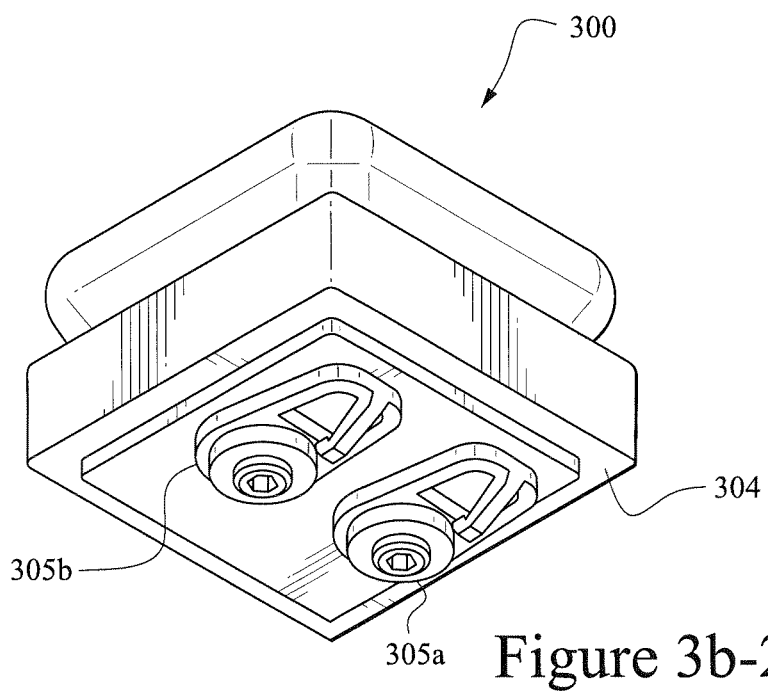

FIGS. 3b-1 and 3b-2 show another diagram of another example embodiment of the medical compression device 300. The example shown in FIG. 3b also has latches 305a, 305b on the back surface 304 of the base portion 301. In this example, the front surface 302 is configured to have an interchangeable portion 303 that can be attached to/removed from the front surface 302. The attachment/removal of such a portion can be accomplished using magnets, for example.

The front surface 302 and the interchangeable portion 303 can be described as a smaller focus contour portion, having a modified half-sphere, for example. Such a design can be advantageous in that it can allow for optimal, more focused pressure in the mid or deep breast region, for example. The design can also allow for more optimal, focused compression in a patient with dense or thick breasts.

Figure 3C:
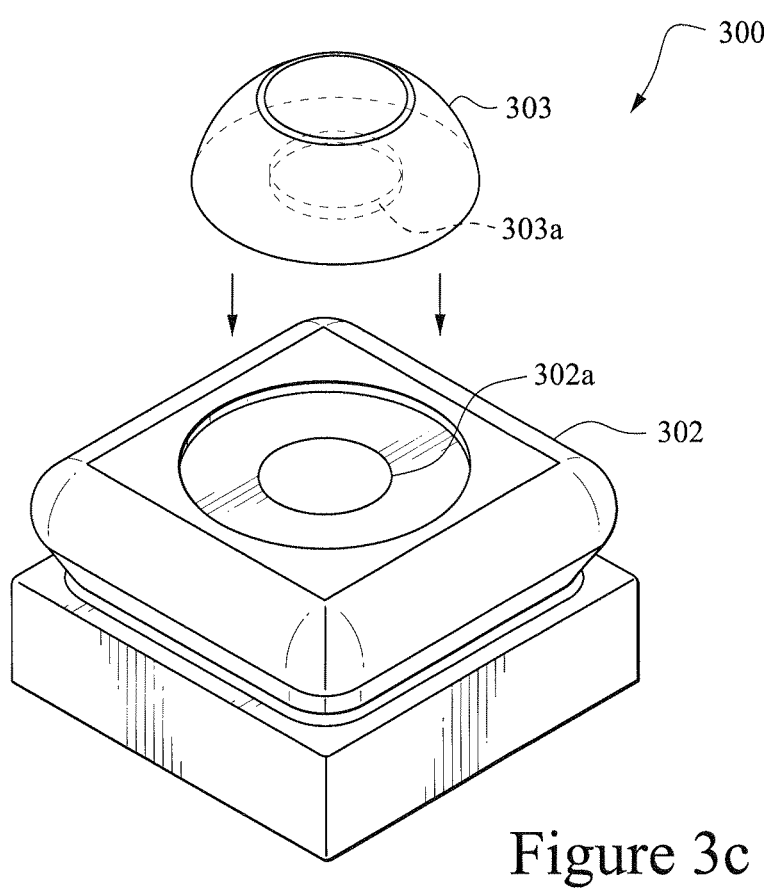
FIG. 3c is a diagram of another example embodiment of the medical compression device using the example interchangeable face component.

FIG. 3c shows another diagram of another example embodiment of the medical compression device 300. FIG. 3c shows the configuration of the device 300 as shown in FIG. 3b, but with the interchangeable portion 303 being removed from the front surface 302 of the device 300. As explained above, the interchangeable portion 303 can connect to the front surface 302 by using magnets 302a and 303a affixed to the front surface 302 and the interchangeable portion 303, respectively.

In the configuration shown in FIG. 3c, the device 300 can be used without the interchangeable portion 303 thereby leaving a relatively flat front surface 302 used for compression. For example, a disc-shaped component having magnets attached to it, for example, can be connected to the front surface 302 forming a unified, flat surface on the device 300. Using a relatively flat front surface 302 can be advantageous in that a larger, less focused field of compression can be applied if more than one biopsy site is to be compressed simultaneously.

Figures 1, 3D:
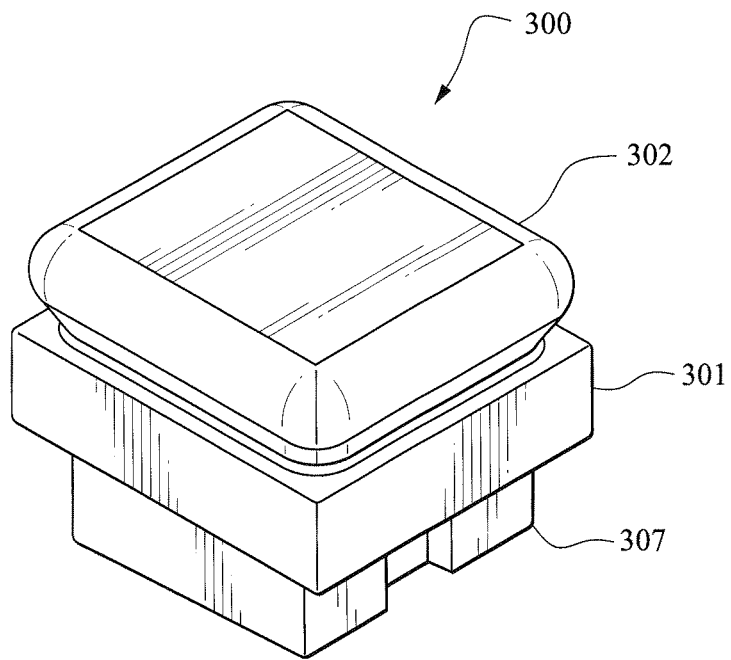
Figures 2, 3D:
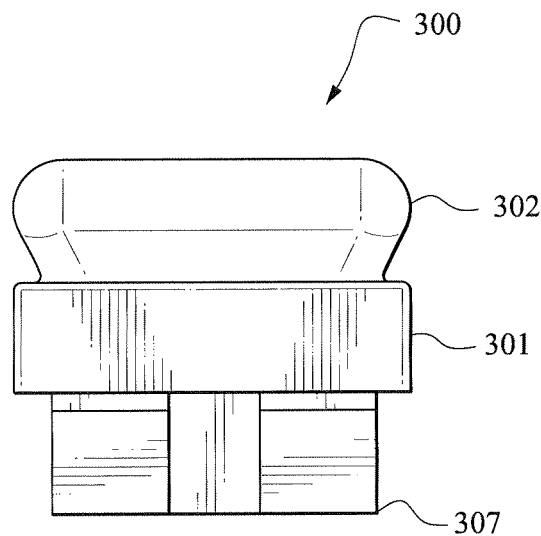

FIGS. 3d-1 and 3d-2 show example diagrams of the device 300 having the large, flat front surface. As can be seen in FIGS. 3d-1 and 3d-2, the front surface 302 is a large, flat front surface that encompasses much of the area of the base portion 301. As explained above, using a relatively flat front surface 302 can be advantageous in that a larger, less focused field of compression can be applied if more than one biopsy site is to be compressed simultaneously. As also explained above, the device 300 using modified half-sphere surface can also act as a large, flat front surface by removing the half-sphere component and/or replacing the half-sphere component with a component to fill the region holding the half sphere (e.g., with a disc portion having magnets). The device 300 in FIGS. 3d-1 and 3d-2 are shown with the latchless design having the attachment portion 307 instead of the latches 305a, 305b. It should be appreciated that the device 300 is in no way limited to the above-mentioned surfaces and can have any form of surface for performing compression.

Figure 4A:
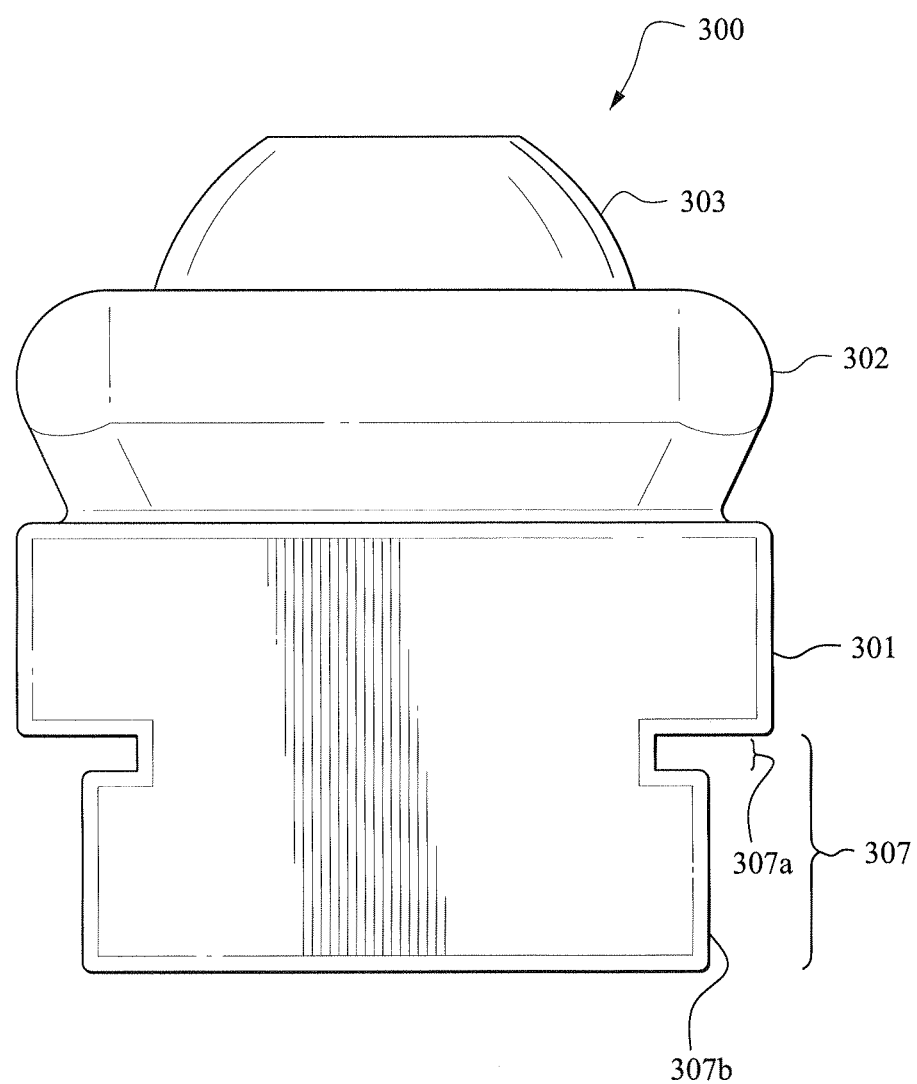
FIG. 4a is a diagram of an example embodiment of the medical compression device without latches.
Figure 4B:
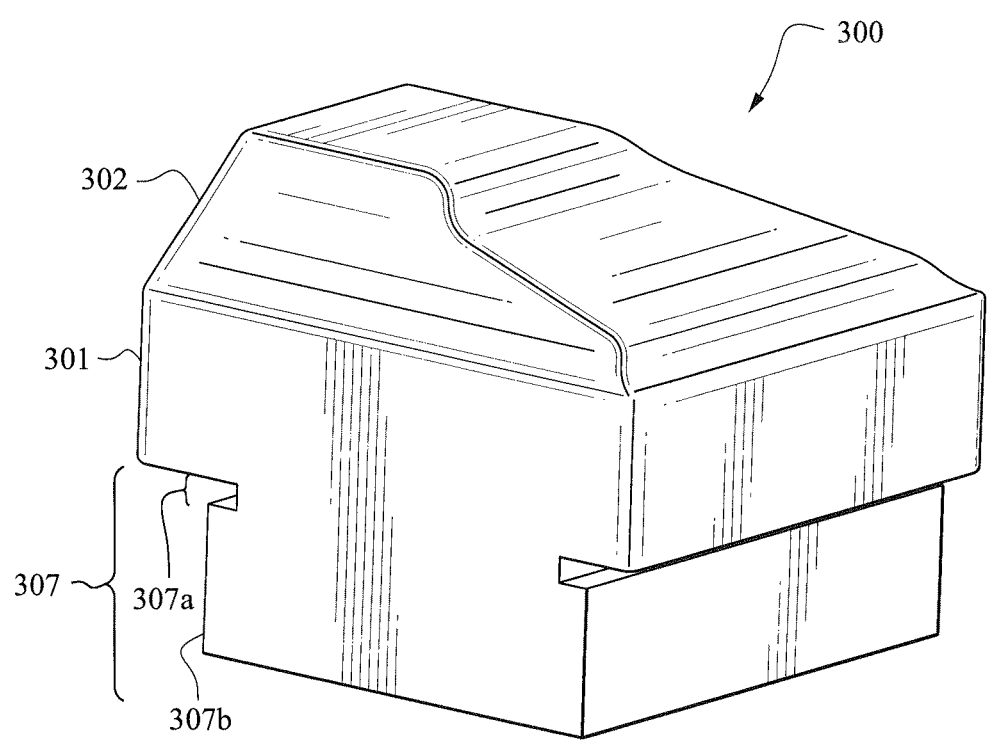
FIG. 4b is a diagram of another example embodiment of the medical compression device without latches.

FIGS. 4a and 4b show example diagrams of a medical compression device 300 designed without latches 305a, 305b. Similar to the device 300 shown in FIGS. 3b and 3c, the device 300 has an interchangeable portion 303, a front surface 302, and a base portion 301. The device 300 in this embodiment also has an attachment portion 307.

The attachment portion 307 can be configured to have a grooved portion 307a and a mounting portion 307b. In this way, the device 300 can connect to the paddle 203 without using any latches 305a, 305b. For example, the device 300 can be inserted into the window 203a of the paddle 203 so that the grooved portion 307a will rest on the paddle 203 as the device 300 sits in the window 203a. In that way, the mounting portion 307b, which can be designed so that it is larger in area than the window 203a, will securely hold the device 300 in the paddle 203 as the mounting portion 307b will not allow the device 300 to fall from the paddle 203. The mounting portion 307b holds the device 300 in place in a similar manner as if the latches 305a, 305b were being used instead of the attachment portion 307.

FIG. 4b shows an example diagram similar to the latch less design shown in FIG. 4a. The device 300 in FIG. 4b has a front surface 302 (similar to the front surface 302 shown in FIG. 3a) and a base portion 301. The front surface 302 can be characterized as a contoured front surface, for example.

In FIG. 4b, connected to the base portion 301 is the attachment portion 307. The attachment portion 307 has a grooved portion 307a and a mounting portion 307b. In this way, the device 300 can connect to the paddle 203 without using any latches 305a, 305b. For example, the device 300 can be inserted into the window 203a of the paddle 203 so that the grooved portion 307a will rest on the paddle 203 as the device 300 sits in the window 203a. In that way, the mounting portion 307b, which can be designed so that it is larger in area than the window 203a, will securely hold the device 300 in the paddle 203 as the mounting portion 307b will not allow the device 300 to fall from the paddle 203. The mounting portion 307b holds the device 300 in place in a similar manner as if the latches 305a, 305b were being used instead of the attachment portion 307.

Figure 5:
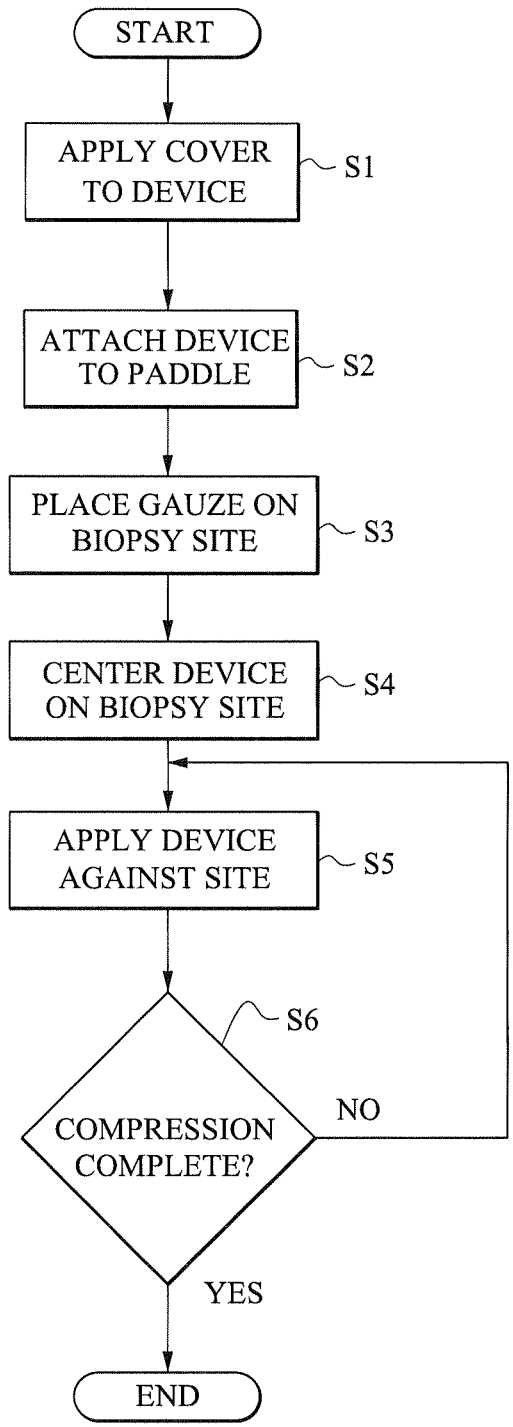
FIG. 5 shows an example embodiment of an application flowchart for using the medical device.

FIG. 5 shows an example embodiment of an application flowchart for using the medical compression device 300 in the medical system 1. It should be appreciated that the process described is not limited to the order of steps described but can be performed in a variety of different orders.

The process begins in step S1 where a user can apply a cover to the device 300. In a preferred embodiment, the cover will be a form of a sterile covering 400 for the device 300. The sterile covering 400 and its application, is discussed further below.

After applying the cover to the device 300, the process proceeds to step S2 where a user can attach the device 300 to the paddle 203. As explained above, the device 300 can be attached to the paddle 203 in a variety of ways. In one embodiment, latches 305a, 305b can be used to secure the device 300 to the paddle 203. In another embodiment, the attachment portion 307 can be used to secure the device 300 to the paddle 203. It should be appreciated that other methods of attaching the device 300 to the paddle 203 are possible and should not be limited to the above-mentioned embodiments.

After the device 300 is attached to the paddle 203, a piece of gauze and/or dressing can be placed on the biopsy site of the patient in step S3. The compression surface of the device 300 is then centered on the biopsy site in step S4. The centering of the compression surface can be accomplished using the controller 201, for example.

After the device is centered, the process proceeds to step S5 where the compression device 300 is applied against the biopsy site. The compression device 300 will remain against the biopsy site (step S6) until compression time is complete. Although not limited to this example, compression time may average 10 to 12 minutes but may be extended as clinically warranted. By advantageously applying the compression using the device 300, the operator can perform other tasks such as cleaning the room and turning it over to the next patient. It should be noted however, that patients should be monitored while the application of the device 300 is occurring and any medical personnel should not leave the patient unattended during the use of the device 300.

Figure 6A:
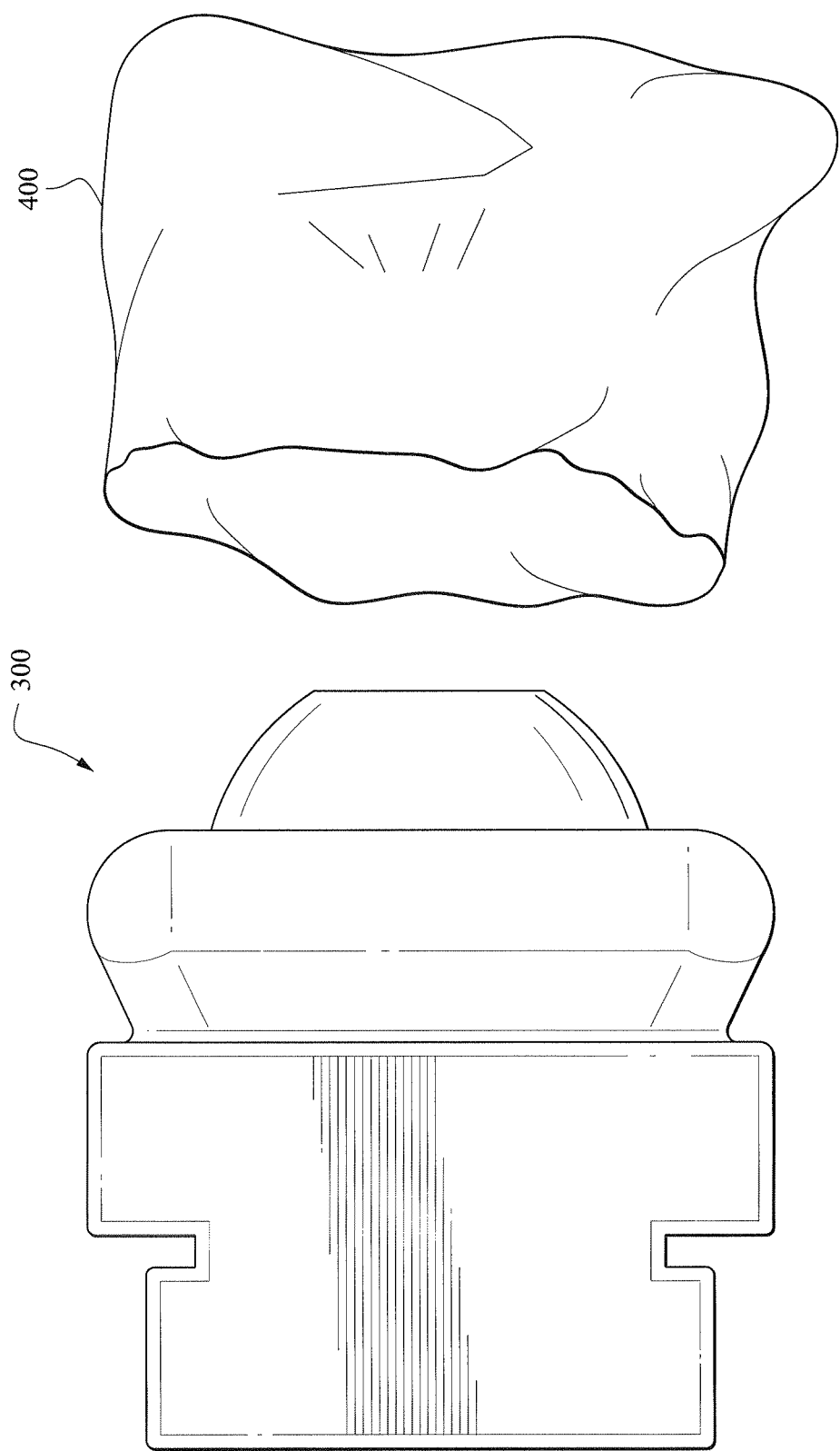
FIG. 6a is a diagram showing the medical compression device with the application of a covering component.
Figure 6B:
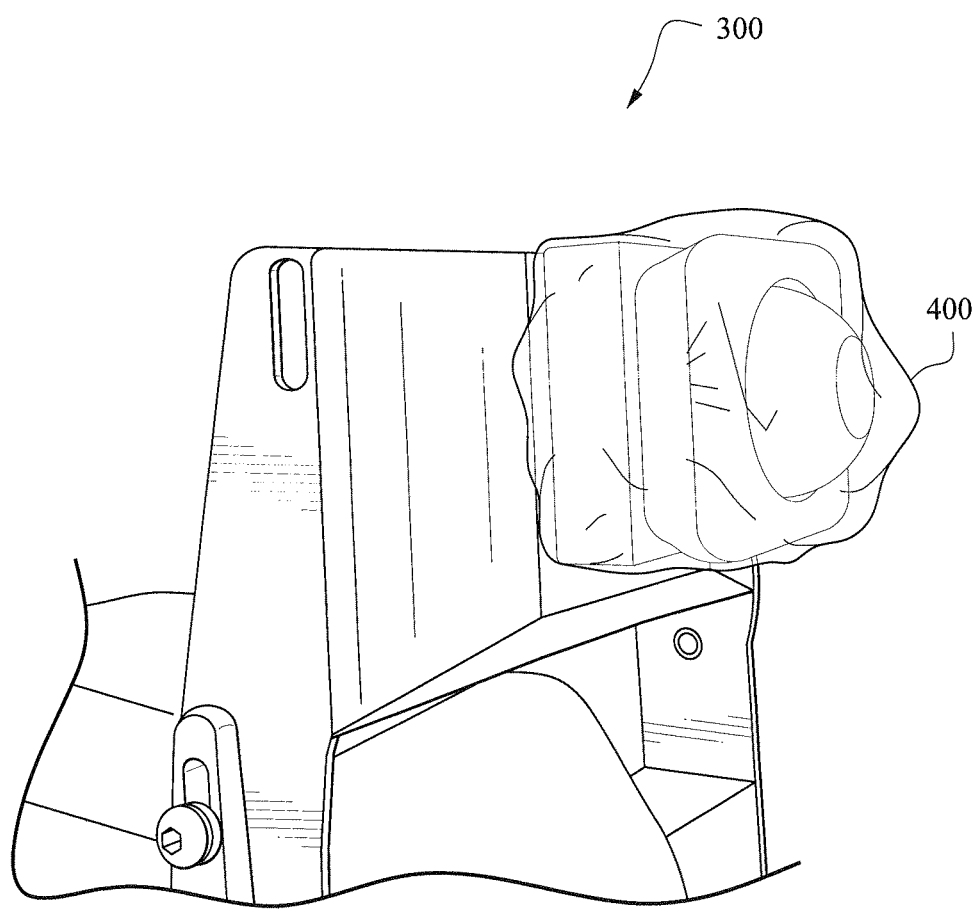
FIG. 6b is a diagram showing an example embodiment of the medical compression device in the biopsy table with the covering component applied to the medical compression device.

FIGS. 6a and 6b show diagrams of another example embodiment of the medical compression device 300. In FIG. 6a, a covering component 400 is used to cover the medical compression device 300. In a preferred embodiment, the covering component 400 is a sterile covering that wraps around, and covers the device 300 while the device 300 is being used. Although not limited to this embodiment, the sterile covering component 400 can be made of a plastic material and can be coated with materials to ensure further sterile use of the device 300. For example, an alcohol based coating or an anti-bacterial based coating can be applied to the covering component 400 to ensure that the covering component 400 remains completely sterile.

It should be appreciated that the device 300 will be used before, during, or after a medical procedure and the application of a sterile covering 400 can be key to ensuring the repetitive use of the device 300. That is, the medical personnel can see a first patient after a biopsy procedure, for example. The medical personnel can use any variation of the device 300 as mentioned above by first applying a sterile covering 400 to the device 300, and then affixing the device 300 in the paddle 203. After applying compression to the biopsy site, the medical personnel can remove the device 300 from the paddle 203 and change the sterile covering 400 with a new, clean sterile covering 400. This allows the medical personnel to continually use the device 300 without having to clean the device 300 or send the device 300 to another facility for cleaning/sterilizing. It should be appreciated that the covering component 400 is not limited to a sterile covering and can be any form of covering. For example, the covering component 400 could also be a cover for transporting or storing the device 300.

FIG. 6b shows a diagram of an example embodiment of the device 300 in the paddle 203 using the covering component 400. As explained above, a sterile covering component 400 is advantageous in that it allows the medical personnel to simply replace a used component 400 with a new, clean component 400 so that the personnel can continually and repetitively use the device 300. It should be appreciated that the sterile covering 400 can simply wrap around the device 300 or can be firmly secured around the device 300 using adhesive to essentially close the covering 400 around the device 300. Of course, the sterile covering 400 is in no way limited to these examples and can be affixed to the device 300 in a variety of ways.

In an ideal case, the medical compression device will use a sterile covering that is approved by the owner/manufacturer of the medical compression device. Given the current state of medical technology, it is unlikely that the medical compression device will ever be used without a sterile covering. However, should the state of medical technology advance to the point where a sterile covering is unnecessary, the medical compression device described herein can then also be used without a sterile covering.

While the technology has been described in connection with what is presently considered to be the most practical and preferred embodiment, it is to be understood that the technology is not to be limited to the disclosed embodiment, but on the contrary, is intended to cover various modifications and equivalent arrangements included within the spirit and scope of the appended claims.

The invention claimed is:

1. A breast-compression device used in relation to a biopsy procedure, comprising:
    a housing having an elongated body and being structurally dimensioned and shaped to be secured to a breast-compression paddle for performing the biopsy procedure, the housing comprising:
    a front portion having a base, a contoured middle portion including a curved surface, and a terminal flattened front surface, the front portion configured to secure and compress the breast of the patient when the breast compression paddle is being operated during the biopsy procedure, wherein the curved surface defines a groove between the base of the front portion and the terminal flattened front surface;
    a base portion operatively coupled to and supporting the front portion, the base portion having a back surface oppositely located to the terminal flattened front surface, the base portion structured to fit within an opening of the breast-compression paddle; and
    a connection portion operatively coupled to the base portion, the connection portion configured to secure the housing of the breast-compression device to the breast-compression paddle at the base portion, the housing of the breast-compression device configured to be releasably attached from the breast-compression paddle by operation of the connection portion.

2. The breast-compression device according to claim 1, wherein the connection portion includes one or more latches, and the device is configured to be inserted into a working window of the paddle and secured to the paddle by positioning the one or more latches such that at least one of the one or more latches overlaps both the working window and a portion of the paddle.

3. The breast-compression device according to claim 1, wherein the terminal flattened front surface is a substantially flat portion.

4. The breast-compression device according to claim 1, further comprising an interchangeable portion that is configured to connect to the terminal flattened front surface.

5. The breast-compression device according to claim 4, further comprising:
    a first connection device configured to connect to the terminal flattened front surface; and
    a second connection device configured to connect to the interchangeable portion,
    wherein the interchangeable portion connects to the terminal flattened front surface by connecting the first connection device to the second connection device.

6. The breast-compression device according to claim 5, wherein the first connection device and the second connection device are magnets.

7. The breast-compression device according to claim 4, wherein the interchangeable portion is a modified half-sphere shaped portion.

8. The breast-compression device according to claim 1, wherein the housing of the breast-compression device is further configured to be covered by a sterile covering.

9. The breast-compression device of claim 1, wherein the middle portion tapers in a direction extending away from the base portion.

10. The breast-compression device of claim 1, wherein the middle portion is contoured such that the width of the front surface decreases as the front surface extends in a direction extending away from the base portion.

11. A breast-compression device, comprising:
    a housing having an elongated body and configured to be secured to a breast-compression paddle for performing a medical procedure related to a breast of a patient, the housing comprising:
    a connection portion located at a first end of the housing and configured to secure the housing of the breast-compression device to the breast-compression paddle, the connection portion including a first groove configured to engage a working window of the breast-compression paddle;
    a base portion operatively coupled to and supporting the connection portion, the base portion located between the first end of the housing and a second end of the housing, the second end of the housing being oppositely located to the first end of the housing; and
    a front portion located at the second end of the housing and having a base, a contoured middle portion, and a terminal flattened front surface, the terminal flattened front surface configured to secure and compress the breast of the patient when the breast-compression paddle is being operated during the medical procedure, the middle portion defining a contoured face that tapers in shape as the face extends away from the base portion towards the second end of the housing,
    wherein the face defines a second groove between the base and the terminal flattened front surface.

12. The device according to claim 11, wherein the connection portion further comprises:
    a mounting portion, wherein the first groove is located between the mounting portion and a point at which the connection portion connects to a back surface portion of the base portion.

13. The device according to claim 12, wherein the device is configured to be inserted into the working window in the paddle and secured to the paddle by affixing the first groove so that at least a portion of the mounting portion overlaps both the working window and a portion of the paddle.

14. The device according to claim 11, wherein the terminal flattened front surface comprises a substantially flat portion.

15. The device according to claim 11, further comprising an interchangeable portion that is configured to connect to the terminal flattened front surface.

16. The device according to claim 15, further comprising:
    a first connection device configured to connect to the terminal flattened front surface; and
    a second connection device configured to connect to the interchangeable portion,
    wherein the interchangeable portion connects to the terminal flattened front surface by connecting the first connection device to the second connection device.

17. The device according to claim 15, wherein the interchangeable portion is a half-sphere shaped portion.

18. The breast-compression device of claim 11, wherein the base portion and the connection portion are substantially rectangular in shape, the connection portion being configured to fit within a rectangular opening of the working window of the breast-compression paddle.

19. A breast-compression device used in relation to a biopsy procedure, comprising:
   a housing having an elongated body and being structurally dimensioned and shaped to be secured to a breast-compression paddle for performing the biopsy procedure, the housing comprising:
      a front portion having a base, a contoured middle portion including a curved surface, and a terminal flattened front surface, the front portion configured to secure and compress the breast of the patient when the breast-compression paddle is being operated during the biopsy procedure, wherein the curved surface defines a groove between the base of the front portion and the terminal flattened front surface;
      a base portion operatively coupled to and supporting the front portion, the base portion structured to conform to a working window of the breast-compression paddle; and
      a connection portion operatively coupled to the base portion, the connection portion configured to be inserted into the working window of the breast-compression paddle to secure the housing of the breast-compression device to the breast-compression paddle.

20. The breast-compression device of claim 19, wherein the housing of the breast-compression device is configured to be releasably attached from the breast-compression paddle by operation of the connection portion.

21. A breast-compression device, comprising:
   a housing having an elongated body and configured to be secured to a breast-compression paddle for performing a medical procedure related to a breast of a patient, the housing comprising:
      a connection portion located at a first end of the housing and having a groove, the connection portion configured to secure the housing of the breast-compression device to the breast-compression paddle, the connection portion including a first groove configured to engage a working window of the breast-compression paddle such that at least a portion of the breast-compression paddle fills the first groove;
      a base portion operatively coupled to and supporting the connection portion, the base portion located between the first end of the housing and a second end of the housing, the groove of the connection portion existing between the base portion and the connection portion; and
      a front portion located at the second end of the housing, the front portion having a base, a contoured middle portion, and a terminal flattened front surface, the terminal flattened front surface configured to secure and compress the breast of the patient when the breast-compression paddle is being operated during the medical procedure,
   wherein a face of the middle portion defines a second groove between the base and the terminal flattened front surface.

22. The breast-compression device of claim 21, wherein the middle portion tapers in shape as the face extends away from the base portion towards the second end of the housing.

* * * * *